United States Patent [19]

Bailey

[11] 4,230,864

[45] Oct. 28, 1980

[54] PROCESS FOR MAKING 5-TRIFLUOROMETHYL PYRIDONE

[75] Inventor: Thomas D. Bailey, Indianapolis, Ind.

[73] Assignee: Reilly Tar & Chemical Corp., Indianapolis, Ind.

[21] Appl. No.: 7,518

[22] Filed: Jan. 29, 1979

[51] Int. Cl.³ .................................................. C07D 213/04
[52] U.S. Cl. .............................. 546/303; 260/343.5; 260/347.91
[58] Field of Search ......................................... 546/303

[56] References Cited

PUBLICATIONS

Hudlicky, Chemistry Of Organic Fluorine Compounds, Sec. Edition, John Wiley & Sons, Pub. p. 158, (1976).

Primary Examiner—Alan L. Rotman

Attorney, Agent, or Firm—Woodard, Weikart, Emhardt & Naughton

[57] ABSTRACT

The chemical compound 5-trifluoromethyl-2-pyrone and a process for preparing a 5-trifluoromethyl-2-oxy compound of the formula

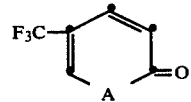

wherein A is oxygen or nitrogen bearing a hydrogen, comprising the step of reacting an amount of the 5-carboxy precursor of the compound with a suitable fluorinating agent to selectively transform the 5-carboxy group without altering the oxygen function in the 2-position of the ring.

7 Claims, No Drawings

PROCESS FOR MAKING 5-TRIFLUOROMETHYL PYRIDONE

BACKGROUND OF THE INVENTION

This invention relates generally to plural-substituted pyridine derivatives and, particularly, to processes for preparing and isolating 5-trifluoromethyl-2-pyridone and for using same.

Although a large number of functionally substituted pyridine compounds are known and capable of synthesis, certain patterns of disubstitution on the pyridine ring are difficult to obtain by any convenient and commercially viable means. Pyridines having functional substituents in the 2- and 5- positions of the ring are often valuable derivatives, but fall within this category. For example, hydroxyl, cyano, carboxy, chloro and other groups are difficult to introduce into these positions on the pyridine ring.

It has long been known that certain non-nitrogen-containing heterocycles can assist in this regard because of their ability to be converted into pyridine bases. Pyrones, pyrilium salts and furans are examples of such transformations. As early as 1884 in Ber., 17, 2384 (1884), Von Pechmann et al. described the conversion of 5-carboxy-2-pyrone to 5-carboxy-2-hydroxypyridine upon treatment with ammonia in the presence of a caustic material such as sodium hydroxide.

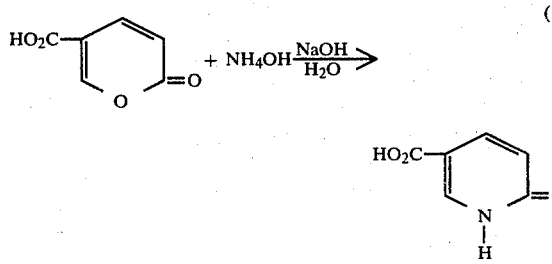
(1)

Although this reaction is potentially useful in some commercial applications, the number of reported uses of the method is small.

This 5-carboxy-2-hydroxypyridine, also known as 6-hydroxynicotinic acid and 5-carboxy-2-pyridone, is an example of a disubstituted pyridine of some commercial value. Besides this Von Pechmann et al. method, it has been prepared directly from a pyridine in two known instances. First, synthesis has been achieved by direct carboxylation of 2-hydroxypyridine, as depicted below.

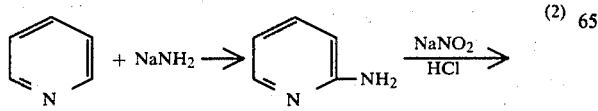
(2)

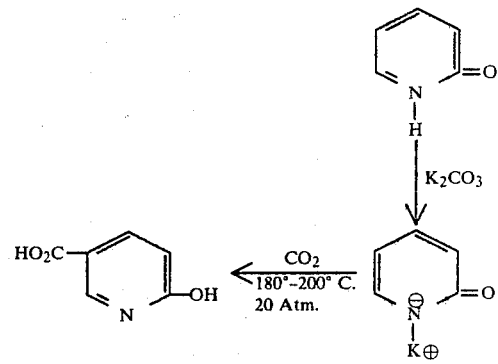

As can be seen, this procedure is rather lengthy and has proven not a viable commercial method. Second, 2-hydroxy-5-carboxypyridine has been prepared directly from 5-carboxypyridine, also known as niacin, through known techniques.

Trifluoromethyl-substituted pyridines have also proven to be valuable derivatives of pyridine bases, although difficult to obtain. Synthesis of these compounds has been accomplished in only a limited number of cases, most of which have involved the conversion of a pyridine carboxylic acid to a trifluoromethyl pyridine utilizing sulfur tetrafluoride.

Accordingly, it is generally known that alkyl and aromatic carboxylic acids react with sulfur tetrafluoride in the presence of hydrogen fluoride to give trifluoromethyl derivatives.

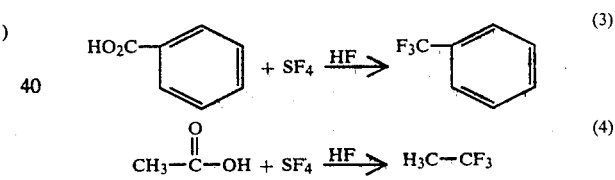
(3)

(4)

This reaction has been applied to amino acids. Kobayashi et al.: *Chem. Pharm. Bull.* 15, 1896 (1967), M. S. Raasch: *J. Org. Chem.*, 27, 1406 (1962). It has also been applied in a few reports to simple pyridine carboxylic acids such as niacin and 3,5-dicarboxypyridine. Kobayashi et al. and Raasch, id.

It is likewise generally known that some esters and anhydrides of these carboxylic acids react with sulfur tetrafluoride to give the corresponding fluorinated ethers. In the case of compounds such as ethyl acetate and dichloromaleic anhydride, the double-bonded oxygen groups are simply replaced during the fluorination reaction. W. R. Hasek, W. C. Smith, and V. A. Engelhardt, *J. Amer. Chem. Soc.*, 82, 543 (1960).

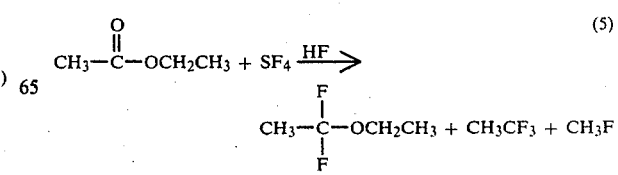
(5)

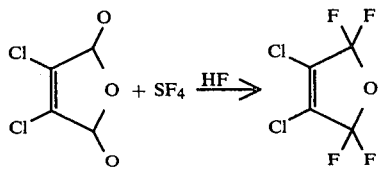  (6)

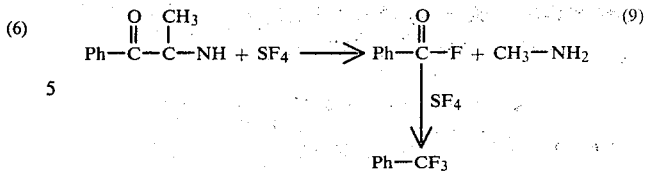  (9)

The presence of a hydroxy group leads to undesirable reactions involving this additional oxygen function in the trifluoromethylation reaction. As used herein, "trifluoromethylation" refers to the conversion of a precursor material to a material containing a trifluoromethyl radical by the addition or substitution of fluorine to the precursor material. As background for this statement, 2- and 4-hydroxypyridines have been shown to physically exist as a mixture of tautomeric forms, appearing both as the hydroxy and the amide derivatives. R. Elderfield, *Heterocyclic Compounds*, 1, 435–440 (1950).

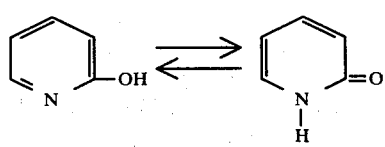  (7)

For this reason, these hydroxypyridines undergo reactions typical of both phenols and amides as also reported in the Elderfield reference.

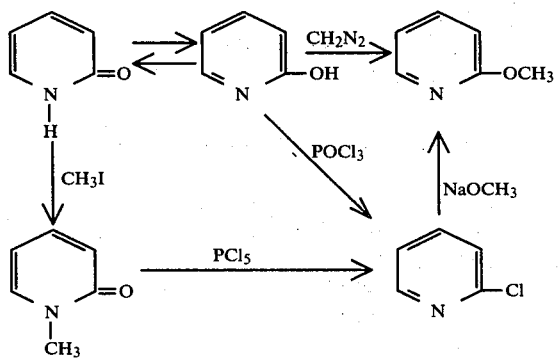

Similar behavior has been reported in substituted hydroxypyridines such as the 5-carboxy-2-hydroxypyridines discussed above. Klingsberg, *Pyridine and Its Derivatives*, Part Three, p. 646 (1962).

It is known that hydroxy groups give rise to fluoro groups by standard substitution upon treatment with sulfur tetrafluoride. Boswell et al., *Org. Reactions*, 21 p. 12 (1973). It is also known that amides react with sulfur tetrafluoride to give a variety of products. Hasel, Smith and Engelhart, *J. Amer. Chem. Soc.*, 82, 543, (1966) For example, if the amide contains at least one nitrogen-hydrogen bond, cleavage at the nitrogen-carbon bond is reported to occur.

This cleavage is believed to be caused by trace amounts of hydrogen fluoride produced during the reaction. Hasek, Smith & Englehart, *J. Amer. Chem. Soc.*, 82, 543 (1966).

Therefore, disubstituted 2- and 5-pyridine derivatives are often difficult to obtain. This statement is particularly true, as taught by the art, with the 2-hydroxy and 5-trifluoromethyl substituents. Nevertheless, 5-trifluoromethyl-2-pyridone is now proving to be a desirable and valuable commercial compound based on both proven and anticipated uses as shown in the art. It appears from the prior art that 5-trifluoromethyl-2-pyridone would be useful as a catalyst in nucleophilic aromatic substitution, formation of amides, and hydrolysis of esters. It also appears from the prior art that 5-trifluoromethyl-2-pyridone would be useful as an antioxidant. Still further, this compound is proving to be a valuable intermediate in the synthesis of herbicides, pharmaceuticals, germicides and the like. See U.S. Pat. No. 4,038,396 to Shen et al. This is due at least in part to the ready substitution for the 2-hydroxy group on the ring and the lower toxicity caused by the 5-trifluoromethyl substituent.

The only reported synthesis of 5-trifluoromethyl-2-pyridone in the art attempts to avoid the prior art problems discussed above. This synthesis, reported in U.S. Pat. No. 4,038,396 issued to Shen et al. on July 26, 1977, teaches a three-step method in Example 111 (beginning at column 23, line 62) for preparing 5-trifluoromethyl-2-pyridone (the tautomeric form of 5-trifluoromethyl-2-hydroxypyridine) from 6-hydroxynicotinic acid. This method includes steps for specifically circumventing the expected interference of the tautomeric hydroxy and amide forms of the initial compound. This is accomplished by converting the 2-substituent to a chloro group in an attempt to protect the 2- position during the trifluoromethylation reaction.

In particular, Shen et al. first teach converting this 6-hydroxynicotinic acid to a less-reactive 6-chloronicotinic acid by a reaction involving liquid phosphorous oxychloride added jointly with solid phosphorous pentachloride and then recaptured in water. The 6-chloro derivative is then subjected to trifluoromethylation using sulfur tetrafluoride in the presence of hydrogen fluoride, and the 2-chloro-5-trifluoromethylpyridine is reconverted back to the hydroxy or amide derivative through a complex treatment under nitrogen with silver acetate in the presence of acetic acid.

This three-step Shen et al. procedure is lengthy and complex, and thus of minimal commercial valuable. It further emphasizes the need for the development of a viable, more efficient process for preparing the valuable 5-trifluoromethyl-2-pyridone.

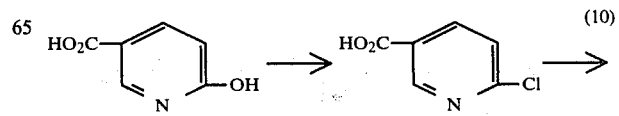  (10)

-continued

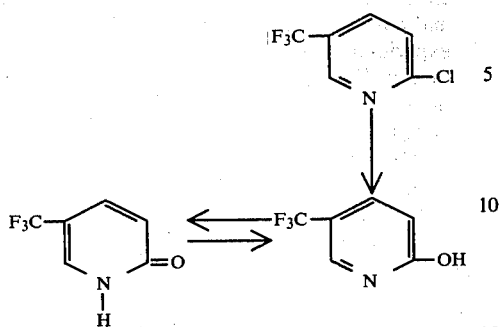

SUMMARY OF THE INVENTION

One aspect of this invention comprises an unexpected process for preparing a 5-trifluoromethyl-2- pyrone or pyridone compound. Beginning with the 5-carboxy precursor of the desired compound, a direct trifluoromethylation is performed by reacting the precursor with a suitable fluorinating agent to selectively transform the 5-carboxy group which contains two oxygen functions to a 5-trifluoromethyl group without altering the oxygen function in the 2-position of the ring.

This new process is completely unexpected and unprecedented in the art. For the pyridone derivative, the tautomeric behavior of 2-hydroxypyridines and the known reactions of sulfur tetrafluoride with both hydroxy compounds and amides provide evidence of unobviousness of this new process. For the pyrone derivative, the prior art likewise provides evidence of unobviousness. Lastly, the Shen et al. reference further demonstrates these prior art teachings. When these teachings are compared to applicant's invention, the unprecedented and unexpected success of applicant's process is made clear. Still further, this process provides two new means for preparing the commercially valuable 5-trifluoromethyl-2-pyridone and its hydroxy form.

A second aspect of this invention is the discovery, isolation and characterization of a new compound, that being 5-trifluoromethyl-2-pyrone as the result of applicant's above process.

DESCRIPTION OF THE PREFERRED EMBODIMENT

As indicated above, one aspect of this invention comprises a process achieving the heretofore unprecedented trifluoromethylation of a 5-carboxy-2-pyrone or 5-carboxy-2-pyridone compound without attack or destruction of the 2-position oxygen function on the aromatic ring. This process further provides two new means for preparing the commercially valuable 5-trifluoromethyl-2-pyridone, the one process proceeding directly to synthesize the pyridone derivative whereas the other process requires the additional step of reacting the new pyrone compound to produce the nitrogen substitution.

Defined broadly, this aspect comprises a process for preparing a 5-trifluoromethyl-2-oxy compound of the formula:

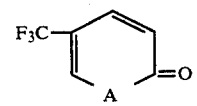

wherein A is oxygen or nitrogen bearing a hydrogen, comprising the step of reacting an amount of the 5-carboxy precursor of the compound with a suitable fluorinating agent to selectively transform the 5-carboxy group without altering the oxygen function in the 2-position of the ring.

In this context, the term "suitable fluorinating agent" is meant to include any known or yet undiscovered fluorine-containing reagent susceptible of forming a trifluoromethyl group when reacted with a carboxy substituent as found on the 5-position of each precursor compound mentioned above. Examples of suitable trifluoromethylating agents presently known include sulfur tetrafluoride, molybdenum hexafluoride, and the like.

Pyridone Trifluoromethylation

In the preferred embodiment of this process, the starting material is an amount of 5-carboxy-2-pyridone, also existing in a 2-hydroxy form and known as 6-hydroxynicotinic acid. As mentioned in the background section of this application, several methods are known in the art for obtaining this compound, as outlined below.

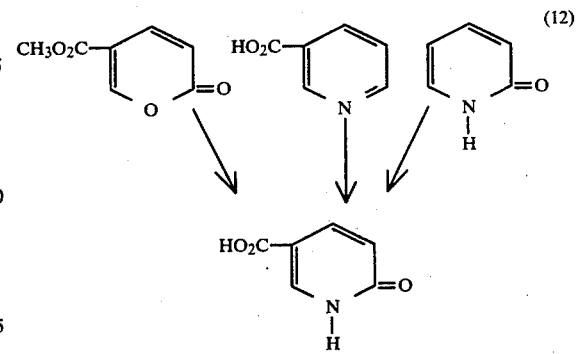

As with the mono-substituted hydroxypyridines, the potential nitrogen-carbon double bond in the pyridone ring of this disubstituted derivative allows a tautomerism, i.e., quasi equilibrium, to exist between the two distinct hydroxy and amide forms.

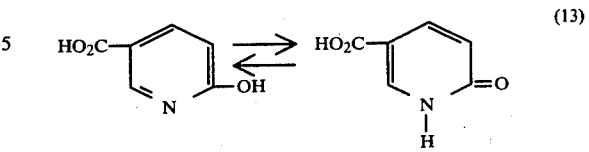

Also, as with the monosubstituted forms, this dual behavior in view of the known reactions of sulfur tetrafluoride with both hydroxy and amide compounds leads to the conclusion that neither the 2-hydroxypyridine or the 2-pyridone forms would be expected to survive trifluoromethylation if this compound were reacted directly with sulfur tetrafluoride under standard conditions. Instead, although not specifically known to occur, this reaction would be predicted from the prior art to cause either hydroxyl displacement or amide cleavage, i.e., destruction of the pyridone form by ring cleavage, both as represented below:

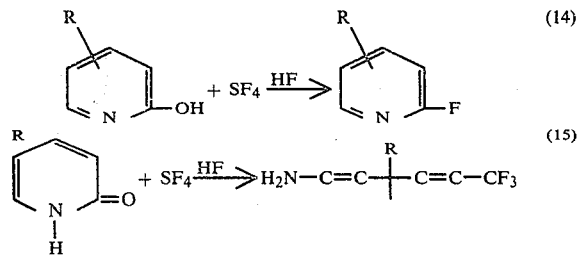

In view of the above, and in view of the report of synthesis in U.S. Pat. No. 4,038,396 specifically circumventing the expected interference with the hydroxy or amide forms, it was completely unprecedented and unexpected that 5-carboxy-2-pyridone reacted directly with sulfur tetrafluoride under laboratory conditions to give the 5-trifluoromethyl-2-pyridone derivative. This reaction is represented below:

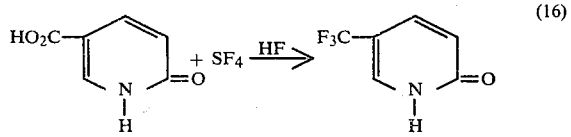

In view of the tautomeric condition that exists between the hydroxy and amide forms, for the remaining portion of this specification and the claims attached hereto, reference will be made only to the amide pyridone form, it being clear that this reference is also meant to include the tautomeric form, unless otherwise specifically indicated.

The preferred conditions of this trifluoromethylation reaction exhibit no significant variance from standard accepted procedures. These conditions are as follows.

An amount of the 2-hydroxy-5-carboxypyridine precursor was first added to a sealed reaction vessel also containing an effective amount of a trifluoromethylating agent. In this context, the agent has been previously defined; and the term "effective amount" is meant to define a sufficient quantity of the agent as determined by stoichiometric or past experimental means to permit the trifluoromethylation reaction to proceed.

The vessel and its contents were then heated to a reaction temperature of between about 60° C. and 150° C. and were maintained at this elevated temperature for a period of between about 6 hours and about 24 hours. The precise temperature and period for the reaction depends, of course, upon many factors including available facilities, reagent concentrations and the desired reaction yields.

As previously stated, the single most important consideration in the reaction is that the conditions are sufficiently mild to allow the trifluoromethylation conversion of the 5-carboxy group without attacking or interfering with the amide function or the 2-position oxygen function on the pyridone ring. In this context, the term "sufficiently mild" is meant to indicate that reaction conditions may exist unknown to applicant and unverified by experiments performed to date that are sufficiently harsh as to prevent trifluoromethylation or to interfere with the reaction as previously taught in the art. These sufficiently harsh conditions, if they exist, are excluded from applicant's invention as described herein and claimed in the attached claims. With this in mind, experiments to date have shown the preferred temperature is 120° C. and the preferred reaction time is 15 hours to achieve a commercially satisfactory yield in excess of 40%.

Although not required, the reaction may proceed in the presence of a catalytic amount of water. It is believed that a small amount of water generates, in situ, a corresponding amount of hydrogen fluoride which serves to accelerate the trifluoromethylation without endangering the success of the reaction. Similarly, the reaction may proceed, if desired, in the presence of a chlorinated hydrocarbon solvent such as chloroform, methylene chloride and the like.

Isolation of the 5-trifluoromethyl-2-pyridone product can then be accomplished by any convenient means. In the preferred method, the reaction mixture after cooling was dissolved into water and its pH adjusted to near neutral, i.e. about pH 7, by addition of a caustic material such as sodium hydroxide, sodium carbonate, potassium carbonate and the like, with sodium hydroxide being preferred. Following this neutralization, the solution was extracted into a suitable solvent that is immiscible in water and easily dissolves the reaction product. Examples of such solvents include chlorinated hydrocarbons, ethers, certain alcohols and aromatic hydrocarbons, with specific examples being chloroform, diethyl ether, 2-butanol and toluene. Evaporation of this extract then gave the 5-trifluoromethyl-2-pyridone product.

Once isolated, this 5-trifluoromethyl-2-pyridone was found to be useful as described in the background section of this application. Still further, it has proven a valuable intermediate in the formation of 2-chloro-5-trifluoromethylpyridine which has proven useful both as an intermediate in herbicide preparation and other uses.

Pyrone Trifluoromethylation

In this second preferred process, the starting material is a 5-carboxy-2-pyrone compound commonly referred to as coumalic acid. This compound is readily synthesized from malic acid in the presence of concentrated sulfuric acid and oleum as represented below.

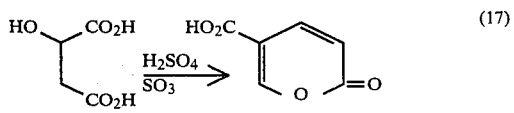

Once formed, this disubstituted pyrone derivative is shown in the prior art to undergo reactions typical of cyclic esters. As previously shown, it is known that other esters react with sulfur tetrafluoride in the presence of hydrogen fluoride to give their fluorinated ether byproducts, the carbonyl oxygen having been replaced by fluorines in the reaction.

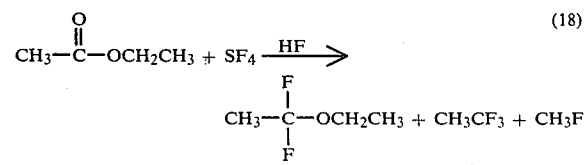

The carboxy pyrone of applicant's preferred process would therefore be expected to react in a similar manner, as suggested by this hypothetical reaction.

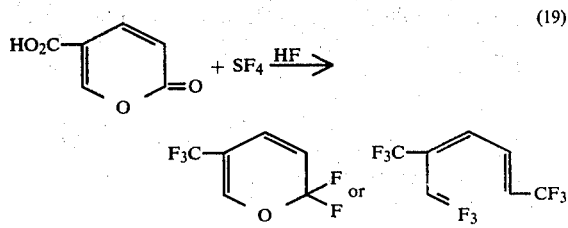
(19)

Formation of the corresponding trifluoromethyl pyrone is unexpected and unprecedented, but is nonetheless accomplished by applicant's preferred process.

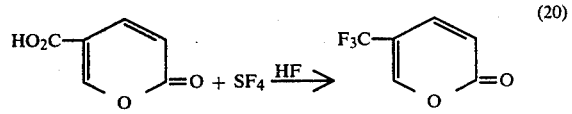
(20)

The conditions of this second trifluoromethylation reaction were identical to those described above in connection with the pyridone transformation. Temperatures were maintained between about 60° and about 150° C., with 120° C. being preferred. The period of the reaction was between about 6 hours and about 24 hours, with 15 hours being preferred. Sulfur tetrafluoride was again the preferred trifluoromethylating reagent; and as above, the reaction can proceed in the presence of either a chlorinated hydrocarbon solvent such as chloroform or a catalytic amount of water, or both if desired. Isolation of the 5-trifluoromethyl-2-pyrone is then accomplished by any convenient means, with the preferred method being that previously described for the pyridone derivative. It is preferred that a purity of at least 60% be obtained.

This 5-trifluoromethyl-2-pyrone is a new compound not previously known to applicant and not identified in any known reference. Its present and potential uses are several. The compound is useful as an extraction solvent. It is also useful as a perfuming agent or air freshening agent, either by itself or in conjunction with other agents. Still further, this new composition readily reacts as normal pyrones with an ammonia-containing agent in the presence of a caustic material to give the similarly valuable 5-trifluoromethyl-2-pyridone derivative previously discussed.

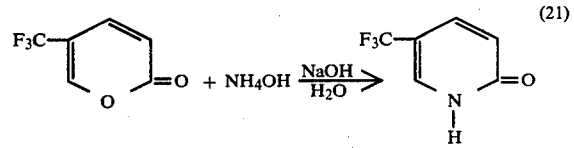
(21)

Examples of acceptable ammonia-containing agents for this reaction include ammonium hydroxide, a solution of ammonia in an alcohol such as methanol, ammonium carbonate and the like. An example of an acceptable and readily available caustic material is sodium hydroxide.

The reaction conditions for this pyrone-to-pyridone conversion were those normally experienced. Temperature was maintained between about 0° C. and about 100° C., with 25° C. being preferred. The period for the conversion was between about 5 minutes and about 2 hours, with 45 minutes being preferred. Isolation of the pyridone product was readily achieved by any convenient means, the preferred method being acidification of the ammonia-caustic solution with a strong mineral acid such as hydrochloric or sulfuric acid and then followed by extraction of the resulting solid. The purity was in excess of 95%. It is preferred that a purity of at least 60% be obtained.

Once isolated, this 5-trifluoromethyl-2-pyridone compound was susceptible of conversion to its 2-chloro-5-trifluoromethylpyridine derivative as described and represented above.

In an effort to promote a better understanding of the principles and scope of this invention, the following specific examples are presented to describe the preparation of specific compounds of this invention using the preferred processes already discussed. These examples are meant to be illustrative only and not restrictive or limiting of the scope of the invention, it being understood that only the preferred embodiments have been shown and described.

EXAMPLE 1

To 50 g of malic acid was added 142 g of concentrated sulfuric acid and 5.8 cc of 65% oleum. The resulting slurry was heated to 100° C. for 1.45 hours. The solution was cooled to 20° C. and 50 g of dry methanol was added. The resulting solution was heated to 100° C. for 1 hour, allowed to cool to room temperature and then poured into 200 cc of cold water. After standing for 0.5 hours, the solution was filtered and the filtrate extracted with chloroform to give, upon evaporation of the solvent, methylcoumalate, mp 68°–71° C.

5 g of this methylcoumalate was slowly added to 10 cc of concentrated ammonium hydroxide and stirred for 1 hour at 25° C. 25 cc of a 50% sodium hydroxide solution was added and the reaction mixture was heated to reflux for 5 minutes. Upon cooling and acidification with concentrated hydrochloric acid, 5-carboxy-2-pyridone was separated and collected by extraction.

To a stainless steel reaction vessel was added 22 g of this 5-carboxy-2-pyridone, 2.8 cc of water and 40 cc of sulfur tetrafluoride. The sealed vessel was heated to 100° C. for 18 hours, cooled to 25° C. and the volatile material vented off. The liquid contents of the bomb were poured into 100 cc of water, the pH adjusted to 7 with sodium carbonate and the neutral solution extracted with chloroform (3×100 cc). The extract was evaporated to dryness to give the 5-trifluoromethyl-2-pyridone product, mp 139°–145° C.

1 g of this 5-trifluoromethyl-2-pyridone was then added to 25 g of 2,4-dinitrochlorobenzene and 40 g piperidine in benzene. It was found that the rate of nucleophilic aromatic substitution of the chloro group by piperidine was increased. After conversion, the 5-trifluoromethyl-2-pyridone was found to be unchanged.

EXAMPLE 2

To 40.3 g of 2-pyridone, also known as 2-hydroxypyridine, dissolved in 200 cc of water was added 100 g of potassium carbonate. The solution was evaporated to dryness, dried at 120° C. for 18 hours and the resulting solid finely ground. To the finely-ground solid was then added 250 cc of mineral oil and the slurry was added to a stainless steel pressure vessel. Carbon dioxide was introduced at 550 psig, and the vessel was heated to 210°–215° C. for 7 hours. The cooled reaction mixture was taken up in 250 cc of hot water, the mineral oil layer removed and the aqueous layer made acidic with concentrated hydrochloric acid. The solid 2-hydroxy-5-carboxypyridine was collected by filtration and dried.

28 g of this 2-hydroxy-5-carboxypyridine was then added to a stainless steel pressure vessel with 20 cc of sulfur tetrafluoride, and the vessel was heated to 100° C. for 24 hours to give the 5-trifluoromethyl-2-pyridone product, mp 144°–147° C., as in Example 1.

2.1 g of this 5-trifluoromethyl-2-pyridone was then added to 100 g of a 10% solution of p-nitrophenyl acetate in dioxane-water and found to accelerate the hydrolysis of the acetate at 20° C. After conversion, the 5-trifluoromethyl-2-pyridone was found to be unchanged.

EXAMPLE 3

To a stainless steel pressure vessel was added 28 g of 2-hydroxy-5-carboxypyridine, as prepared in Example 1. Forty cc of sulfur tetrafluorde were then added to the vessel and the sealed bomb was heated to 145° C. for 12 hours to once again give the 5-trifluoromethyl-2-pyridone product, as in Example 1.

25 g of this 5-trifluoromethyl-2-pyridone was then added to 100 cc of phosphorous oxychloride and 40 g of phosphorous pentachloride and heated to 100° C. to 8 hours, the excess phosphorous oxychloride removed by distillation at reduced pressure and the residue remaining taken up in 200 cc of water. The pH was adjusted to 7 with sodium hydroxide. Extraction of the solution three times with 100 cc of with chloroform gave 2-chloro-5-trifluoromethylpyridine on removal of the solvent.

EXAMPLE 4

To 200 g of malic acid was added 175 cc of concentrated sulfuric acid and 1 g of 65% oleum. The mixture was heated to 100° C. for two hours, cooled to 30° C. and diluted with 300 cc of water. The reaction mixture was cooled to 25° C. and filtered to give coumalic acid.

28 g of this coumalic acid was then placed in a stainless steel pressure vessel along with 1.8 cc of water, and 20 cc of sulfur tetraflouride was then distilled into the vessel. The reactor was heated to 120° C. for 15 hours, cooled to 20° C. and the gaseous materials vented off. The pressure vessel was then opened and the contents poured into 300 cc of water. The pH of this aqueous solution was adjusted to 7 by adding sodium carbonate, and the neutral solution was extracted with chloroform (3×100 cc). The chloroform extracts were dried over magnesium sulfate, evaporated under reduced pressure and distilled at reduced pressure to give a new compound. This compound was isolated and characterized as 5-trifluoromethyl-2-pyrone, bp 77°–79° C. at 12 mm Hg, using standard spectroscopic and analytical methods. The purity was in excess of 95%.

This new 5-trifluoromethyl-2-pyrone compound was then used to effectively extract pyridine bases from aqueous solution.

EXAMPLE 5

To 2 cc of concentrated ammonium hydroxide was added 0.1 g of this new 5-trifluoromethyl-2-pyrone compound isolated in Example 4 and the mixture was stirred for 0.5 hours. The mixture was cooled to 20° C., 1 cc of 50% sodium hydroxide solution was added and the mixture then boiled for 5 minutes. The solution was cooled to 20° C., diluted with 5 cc of water and the pH adjusted to 4 with concentrated hydrochloric acid. The solution was extracted with diethyl ether (3×25 cc), and the extract was evaporated under reduced pressure to give 5-trifluoromethyl-2-pyridone, mp 142°–145°, as in Example 1.

EXAMPLE 6

25 g of coumalic acid obtained as in Example 4 was placed in a stainless steel bomb, 2.5 g of anhydrous hydrofluoric acid and 20 cc of sulfur tetrafluoride were added and the mixture was heated to 140° C. for 12 hours. Isolation and characterization as in Example 4 identified the reaction product as 5-trifluoromethyl-2-pyrone.

This 5-trifluoromethyl-2-pyrone was found to be an effective air freshener when formulated with a suitable germicidal base. The product had a pleasant, characteristic sweet, musk-like odor.

EXAMPLE 7

28 g of coumalic acid obtained as in Example 4 was placed in a stainless steel bomb, 20 cc of sulfur tetrafluoride was added and the vessel heated to 120° C. for 15 hours to give 5-trifluoromethyl-2-pyrone. Treatment with ammonium hydroxide and sodium hydroxide as in Example 5 then gave the 5-trifluoromethyl-2-pyridone reaction product, its tautomeric form being 2-hydroxy-5-trifluoromethylpyridine.

The invention claimed is:

1. A process for preparing 5-trifluoromethyl-2-pyridone comprising the step of reacting an amount of 2-hydroxy-5-carboxypyridine with a suitable fluorinating agent to selectively transform the 5-carboxy group without altering the oxygen function in the 2-position of the ring.

2. The process in claim 1 wherein said reacting is at a temperature of between about 60° C. and about 150° C.

3. The process in claim 2 wherein said reacting is for a period of between about 6 hours and about 24 hours.

4. The process in claim 1 wherein said reacting is in the presence of a chlorinated hydrocarbon solvent.

5. The process in claim 1 wherein said reacting is in the presence of a catalytic amount of water.

6. The process in claim 2 wherein the fluorinating agent is sulfur tetrafluoride.

7. The process in claim 6 wherein said reacting is at a temperature of about 120° C. and for a period of about 15 hours.

* * * * *